United States Patent
Chung

(10) Patent No.: US 11,123,216 B2
(45) Date of Patent: Sep. 21, 2021

(54) CONDOM FOR PATIENTS WITH ERECTILE DYSFUNCTION

(71) Applicant: UFU HEALTH CO., LTD., Seoul (KR)

(72) Inventor: Kyung Jin Chung, Seoul (KR)

(73) Assignee: UFU HEALTH CO., LTD., Seoul (KR)

(*) Notice: Subject to any disclaimer, the term of this patent is extended or adjusted under 35 U.S.C. 154(b) by 385 days.

(21) Appl. No.: 16/330,394

(22) PCT Filed: Sep. 5, 2017

(86) PCT No.: PCT/KR2017/009670
§ 371 (c)(1),
(2) Date: Mar. 5, 2019

(87) PCT Pub. No.: WO2018/044132
PCT Pub. Date: Mar. 8, 2018

(65) Prior Publication Data
US 2021/0228398 A1      Jul. 29, 2021

(30) Foreign Application Priority Data
Sep. 5, 2016    (KR) .................. 10-2016-0113844

(51) Int. Cl.
*A61F 5/41*       (2006.01)
*A61F 6/04*       (2006.01)
*A61M 37/00*      (2006.01)

(52) U.S. Cl.
CPC .................. *A61F 5/41* (2013.01); *A61F 6/04* (2013.01); *A61M 37/0015* (2013.01);
(Continued)

(58) Field of Classification Search
CPC .... A61F 5/41; A61F 6/02; A61F 6/04; A61M 37/0015; A61M 2037/0023
See application file for complete search history.

(56) References Cited

U.S. PATENT DOCUMENTS 4,829,991 A     5/1989  Boeck
5,626,149 A *   5/1997  Schwartz .................. A61F 5/41
                                                    128/842
(Continued)

FOREIGN PATENT DOCUMENTS

JP    2009-195684 A    9/2009
KR    20-0200631 Y1   10/2000
(Continued)

OTHER PUBLICATIONS

International Search Report for PCT/KR2017/009670 dated Feb. 14, 2018 (5 pages).

*Primary Examiner* — John P Lacyk
(74) *Attorney, Agent, or Firm* — Sughrue Mion, PLLC

(57) ABSTRACT

The present invention relates to a functional condom that enables a patient with erectile dysfunction to have normal sexual intercourse and, more particularly, to a condom including a micro-needle (13) provided on an inner surface of an upper portion (10), wherein the micro-needle (13) contains a drug (P) that is an erection-inducing substance. According to the present invention, patients, including those for whom pharmacotherapy is not possible due to side effects or due to a lack of therapeutic effect, may resolve erectile dysfunction without the use of painful injection therapy, by simply wearing the condom.

14 Claims, 4 Drawing Sheets

(52) U.S. Cl.
CPC ... *A61F 2005/414* (2013.01); *A61F 2006/048* (2013.01); *A61M 2037/0023* (2013.01); *A61M 2210/167* (2013.01)

(56) References Cited

U.S. PATENT DOCUMENTS

| | | | | |
|---|---|---|---|---|
| 6,007,836 | A | * | 12/1999 | Denzer ................ A61F 6/04 128/842 |
| 6,145,507 | A | | 11/2000 | Hardy |
| 2007/0175484 | A1 | | 8/2007 | Staab |
| 2012/0305004 | A1 | | 12/2012 | Levy |
| 2015/0320586 | A1 | | 11/2015 | Nguyen et al. |

FOREIGN PATENT DOCUMENTS

| | | |
|---|---|---|
| KR | 10-2004-0059583 A | 7/2004 |
| KR | 10-2007-0042687 A | 4/2007 |
| KR | 10-1410468 B1 | 6/2014 |
| WO | 2009/073809 A2 | 6/2009 |
| WO | 2014/132240 A1 | 9/2014 |

* cited by examiner

CONDOM FOR PATIENTS WITH ERECTILE DYSFUNCTION

TECHNICAL FIELD

The present invention relates to a functional condom which enables a patient with erectile dysfunction to have normal sexual intercourse.

BACKGROUND ART

Erectile dysfunction, i.e., impotence, means a male sexual dysfunction in which the penis fails to become erect or stay erect so as to have sexual relations. Erectile dysfunction may cause personal problems, such as frustration, sterility, loss of confidence, conflicts with spouses and physiological discouragement, social problems, such as family discord, etc.

As conventional treatment methods for erectile dysfunction, there are pharmacotherapy in which drugs for erectile dysfunction, such as Viagra, are taken orally, injection therapy in which drugs for treatment erectile dysfunction are injected directly into the testes or the penis, a drug injection method into the urethra, a method for inserting a penis prosthesis, etc.

Pharmacotherapy is convenient and effective, but it has been reported that a large number of patients undergoing pharmacotherapy experienced side effects, such as facial flushing, headache, etc., and, thereamong, about 10-44% of patients experienced little effect and thus treatment failed.

If pharmacotherapy is ineffective, injection therapy in which a patient directly injects an erection inducing drug into the penis by his own hand is used, and such an aseptic self-injection method is difficult to learn and inject an accurate dose of the drug, and causes pain. When an excessive dose of the drug is injected, a risk of fatal side effects which may cause damage to sexual organs, such as priapism, etc., is increased, and, when the drug is repeatedly injected to the body of the penis, there may be a possibility of curving the penis due to fibrosis of the penis.

In the case of treatment for erectile dysfunction by the drug injection method into the urethra, an erection inducing drug absorbed into the corpus spongiosum through the urethra is transmitted to the corpus cavernosa through vein connection passages and thus causes erection, and such a method requires a patient to urinate prior to drug injection so as to maintain moisture in the urethra and then to inject the drug into the urethra and thus causes patient cumbersomeness and inconvenience.

Hereinafter, the related art will be described.

Korean Registered Patent No. 10-1410468 relates to an improved condom, disclosing technology in which a vasodilator is provided to the inside of the condom and thus, when a user wears the condom, the vasodilator is absorbed into the epidermis of the penis to provide effects, such as erectile dysfunction treatment and prevention of premature ejaculation, but the drug is absorbed just through the epidermis and thus erectile dysfunction treatment effects are decreased.

Further, Korean Patent Laid-open Publication No. 2007-0042687 relates to a condom for sexually disabled persons, disclosing a condom device which improves erectile dysfunction through formation of a vacuum within the condom using an air suction pump, but, in this case, a blood flow is blocked so as to maintain erection and thus causes unnatural performance and problems, such as cooling of the penis, tissue damage, thrombosis, etc.

(Patent Document 1) KR 10-1410468 B
(Patent Document 2) KR 2007-0042687 A

DISCLOSURE

Technical Problem

Therefore, the present invention has been made in view of the above problems, and it is an object of the present invention to provide a functional condom which may comparatively simply solve erectile dysfunction without use of oral pharmacotherapy, which may cause side effects and be ineffective, and self-injection therapy, which may be difficult for a user to learn and be painful.

Technical Solution

In accordance with the present invention, the above and other objects can be accomplished by the provision of a condom including an upper portion (10) configured to cover a glans of a user's penis, extending downwards and provided with micro-needles (13) provided on an inner surface thereof, a lower portion (20) connected to the upper portion (10) and extending downwards, and a tightening part (30) provided at a lower end of the lower portion (20) and configured to adhere and fix the upper portion (10) and the lower portion (20) to the penis when the condom is worn on the penis, wherein the micro-needles (13) includes a drug (P) corresponding to an erection inducing substance.

The upper portion (10) may extend downwards such that a radius thereof is gradually increased, and the lower portion (20) may have a greater radius than the radius of the upper portion (10) and extend downwards.

The upper portion (10) may be formed of an elastic material.

The condom may further include an intermediate tightening part (40) located between the upper portion (10) and the lower portion (20) and configured to adhere and fix the upper portion (10) to the glans.

The intermediate tightening part (40) may include a plurality of protrusions (41) protruding to the outside of the condom.

The drug (P) may be one selected from the group consisting of prostaglandin (E1), papaverine and phentolamine, or be a mixture of two or more selected from the group consisting of prostaglandin (E1), papaverine and phentolamine.

The condom may have a bell shape when inflated.

An opening (19) may be located at a distal end tip of the upper portion (10).

The micro-needles (13) may be located only at a designated angle radially from a center of the upper portion (10).

The micro-needles (13) located only at the designated angle radially from the center of the upper portion (10) may be inserted into the glans except for a urethral meatus of the glans.

The micro-needles (13) may be formed of a biodegradable material.

The condom may further include a micro-needle cover (14) detachably attached to the micro-needles (13) so as to cover the micro-needles (13).

When the condom is worn on the penis, the micro-needles (13) may be adhered to the glans, and the erection inducing substance may be injected into corpus spongiosum of the glans, be then transmitted to corpus cavernosa through vein connection passages between the corpus spongiosum and the corpus cavernosa and thus cause erection.

The tightening part (30) may prevent blood in the penis from returning to the inside of a systemic vein and thus increase a residence time of the injected erection inducing substance in the penis.

Advantageous Effects

According to the present invention, patients which cannot use pharmacotherapy due to side effects or due to a lack of therapeutic effect, may solve erectile dysfunction simply by wearing a condom without use of painful injection therapy.

Since a drug is administered directly to the corpus spongiosum in the glans by microneedles and may thus act very fast, a patient may have a satisfactory sex life just by wearing the condom according to the present invention just before sexual intercourse. Thereby, not only personal problems, such as loss of confidence, but also social problems, such as family discord, may be solved.

Various embodiments of the present invention are possible. A condom according to one embodiment may implement an original function thereof, i.e., a contraception function, to avoid undesired pregnancy and reduce the risk of sexually transmitted diseases, and a condom according to another embodiment may remove the contraception function and thus solve subfertility caused by erectile dysfunction. Further, a condom according to yet another embodiment may further include a sexual device configured to increase sexual satisfaction using an intermediate tightening part.

Further, in the condom implementing the contraception function, a removable microneedle cover is provided and thus prevents microneedles from damaging the condom.

In addition, in the condom implementing the contraception function, the microneedles provided on the condom are formed of a biodegradable substance and thus solve damage to the skin of a sexual organ due to friction during sexual relations.

If the condom provided with the microneedles according to the present invention is repeatedly used, the microneedles may repeatedly irritate the glans and thus assist treatment of premature ejaculation.

BEST MODE

Hereinafter, condoms according to various embodiments of the present invention will be described with reference to the accompanying drawings.

In FIGS. 1 to 4, an upper region of each figure (i.e., one closed side of a condom) is referred to as an upper portion and a lower region of each figure (i.e., the other open side of the condom) is referred to as a lower portion.

Hereinafter, the term "condom" may include not only a bell-shaped condom covering a man's penis during sexual intercourse so as to avoid unwanted pregnancy or prevent sexually transmitted diseases but also all types of condoms formed of elastic materials which may be adhered to the man's penis, such as a type of condom, one side of which is open to allow impregnation (with reference to FIG. 3), a type of condom which is not blown up during expansion, and a band-type or plate-type condom.

Embodiment 1

Figure 1:
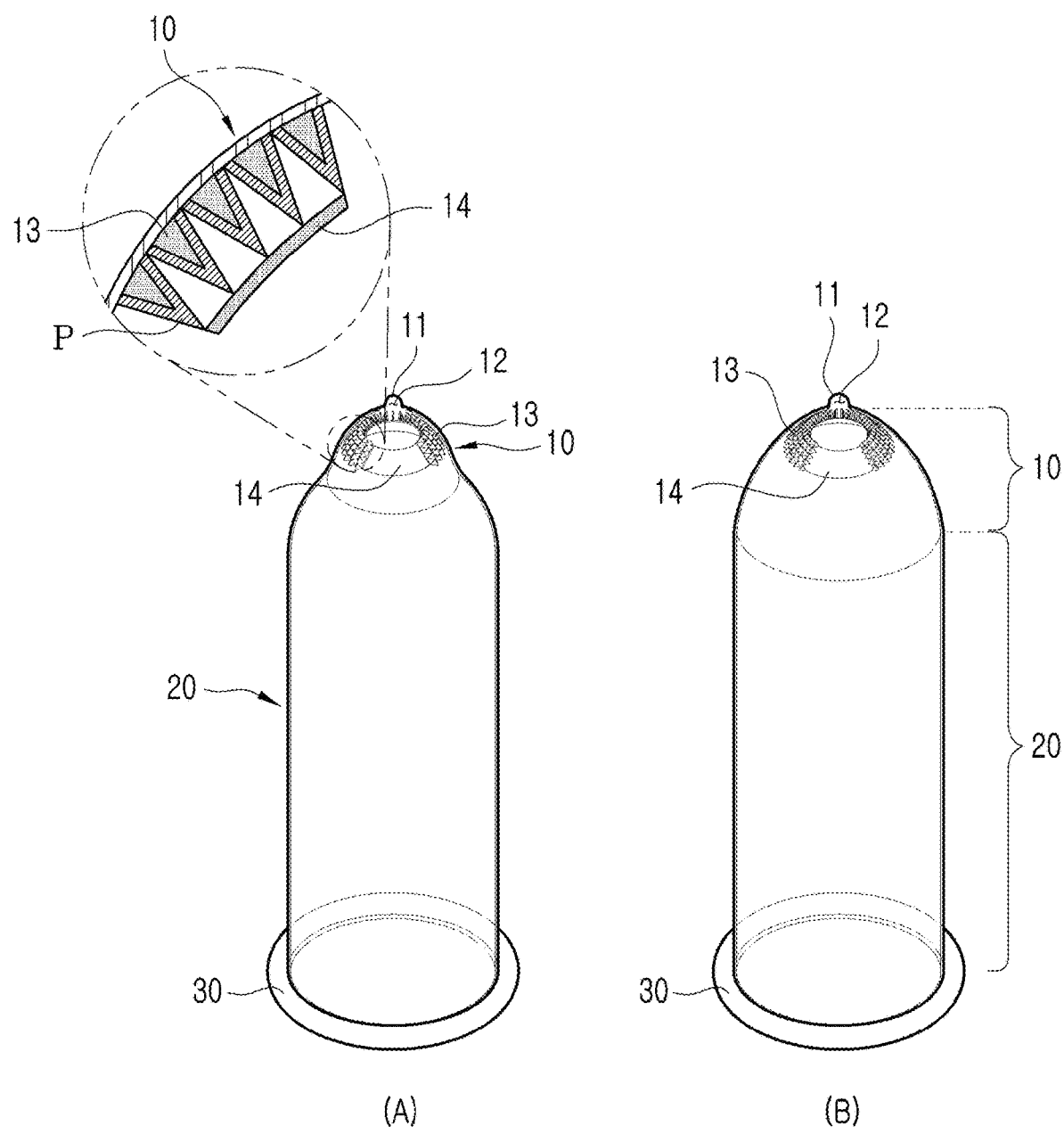
FIG. 1 is a view illustrating condoms according to embodiment 1 of the present invention.

Referring to FIG. 1, a condom according to embodiment 1 will be described.

The condom according to embodiment 1 includes an upper portion (10), a lower portion (20) and a tightening part (30). Here, the upper portion (10) is a portion of the condom surrounding the glans of a man's penis when the condom is worn on the penis.

Although FIG. 1(A) exemplarily illustrates the condom in which the upper portion (10) and the lower portion (20) are provided divisionally, the upper portion (10) and the lower portion (20) may be formed integrally with each other so as to be connected as one unit without a boundary therebetween, as exemplarily shown in FIG. 1(B).

Similarly to conventional condoms, a distal end tip (11) is located at an upper end of the upper portion (10), and a receiving part (12) to receive semen is provided within the distal end tip (11). Further, the tightening part (30) is a ring formed of a flexible material, which is located at a lower end of the condom, and the tightening part (30) is provided at a lower end of the lower portion (20) and serves to adhere and fix the upper portion (10) and the lower portion (20) to the penis when the condom is worn on the penis. Further, the tightening part (30) prevents blood in the penis from returning to the inside of the systemic vein and thus causes an injected erection induction agent to stay in the penis for a long time, thereby more effectively inducing erection. Of course, the tightening part (30) may also function to maintain sealing of the condom so as to prevent the semen from flowing down to the outside of the condom, in the same manner as tightening parts of the conventional condoms.

Micro-needles (13) are provided on the inner surface of the condom according to the present invention. Hereinafter, the micro-needles (13) will be described in detail.

The glans has a very simple structure including three layers, i.e., the stratified squamous epithelium having a 5 to 6 cell layered structure which is keratinized and located as the outermost layer, the lamina propria which is a loose connective tissue having a thickness of 1-2 mm located under the stratified squamous epithelium, and the corpus spongiosum which is located as the innermost layer such that the volume thereof is expanded by blood introduced thereinto. The above histological property of the glans in which the corpus spongiosum is located directly under the lamina propria having a small thickness allows an erection inducing substance to be effectively and rapidly injected into the corpus spongiosum.

Through the drug injection method into the urethra, it was already proved that an erection inducing substance injected into the corpus spongiosum is transmitted to the corpus cavernosa through vein connection passages between the corpus spongiosum and the corpus cavernosa and thus causes erection.

The micro-needles (13) include a drug (P) corresponding to an erection inducing substance. When a user wears the condom according to the present invention, the microneedles (13) come into contact with the user's glans even if the user does not take a specific action and, thus, the erection inducing substance is administered to the glans. Therefore, as compared to the conventional self-injection therapy into the penis, the condom according to the present invention has the same advantage as in the conventional self-injection therapy, i.e., speediness in exhibition of effects, but eliminates the drawbacks of the conventional self-injection therapy, i.e., the necessity of proficiency in injection or pain caused by injection.

Here, the drug (P) corresponding to the erection inducing substance may be one selected from the group consisting of prostaglandin (E1), papaverine and phentolamine, or be a mixture of two or more selected from the group consisting of prostaglandin (E1), papaverine and phentolamine. For example, the drug (P) may be a bi-mixed drug of papaverine and phentolamine or a tri-mixed drug of papaverine, phentolamine and prostaglandin (E1), or include any substance which may induce erection, without being limited thereto.

The micro-needles (13) may be coated with the drug (P) or the drug (P) may be stored in the micro-needles (13), and the micro-needles (13) may include the drug (P) in any way.

Since the micro-needles (13) should administer the drug (P) directly to the glans, the micro-needles (13) may be provided at the upper portion (10) rather than at the lower portion (20) of the condom. Therefore, the drug (P) administered by the micro-needles (13) is injected into the corpus spongiosum of the glans, is transmitted to the corpus cavernosa through the vein connection passages between the corpus spongiosum and the corpus cavernosa and thus causes erection.

Since, when the micro-needles (13) come into contact with the user's urethral meatus, the micro-needles (13) may cause side effects, such as urethral injury, dysuria, urethral stricture, etc., the micro-needles (13) should not come into contact with the urethral meatus. Therefore, the micro-needles (13) should not be provided at a part of the condom corresponding to the user's urethral meatus. For this purpose, the micro-needles (13) are provided only at a part of the inner surface of the upper portion (10) located radially at a designated angle. Referring to FIG. 4(C), the micro-needles (13) should not be located at a part of the inner surface of the upper portion (10) placed between about the 4 o'clock position and the 6 o'clock position when you look at the user from the front.

Since the micro-needles (13) may be rubbed against the skin of the penis several times due to friction during sexual intercourse and thus damage the skin of the penis, the micro-needles (13) may be formed of a biodegradable material so as to be degraded or be absorbed into the skin of the penis simultaneously with injection of the drug (P) into the glans after wearing the condom.

Further, contraception failure due to tearing of the condom by sharp tips of the micro-needles (13) should be prevented. Therefore, a micro-needle cover (14) formed of a soft material may be provided at the front ends of the micro-needles (13) so as to prevent tearing of the condom during packaging and distribution of the condom. When using the condom according to the present invention, the user removes the micro-needle cover (14) and then uses the condom (referring to FIGS. 4(B) and 4(C)).

If the condom according to the present invention is continuously used, the micro-needles (13) may repeatedly irritate the glans. Therefore, the condom according to the present invention has excellent effects on not only treatment of erectile dysfunction but also treatment of premature ejaculation.

Further, similarly to conventional condoms, the inner surface of the upper portion (10) may be coated with a spermicide.

Figure 4:
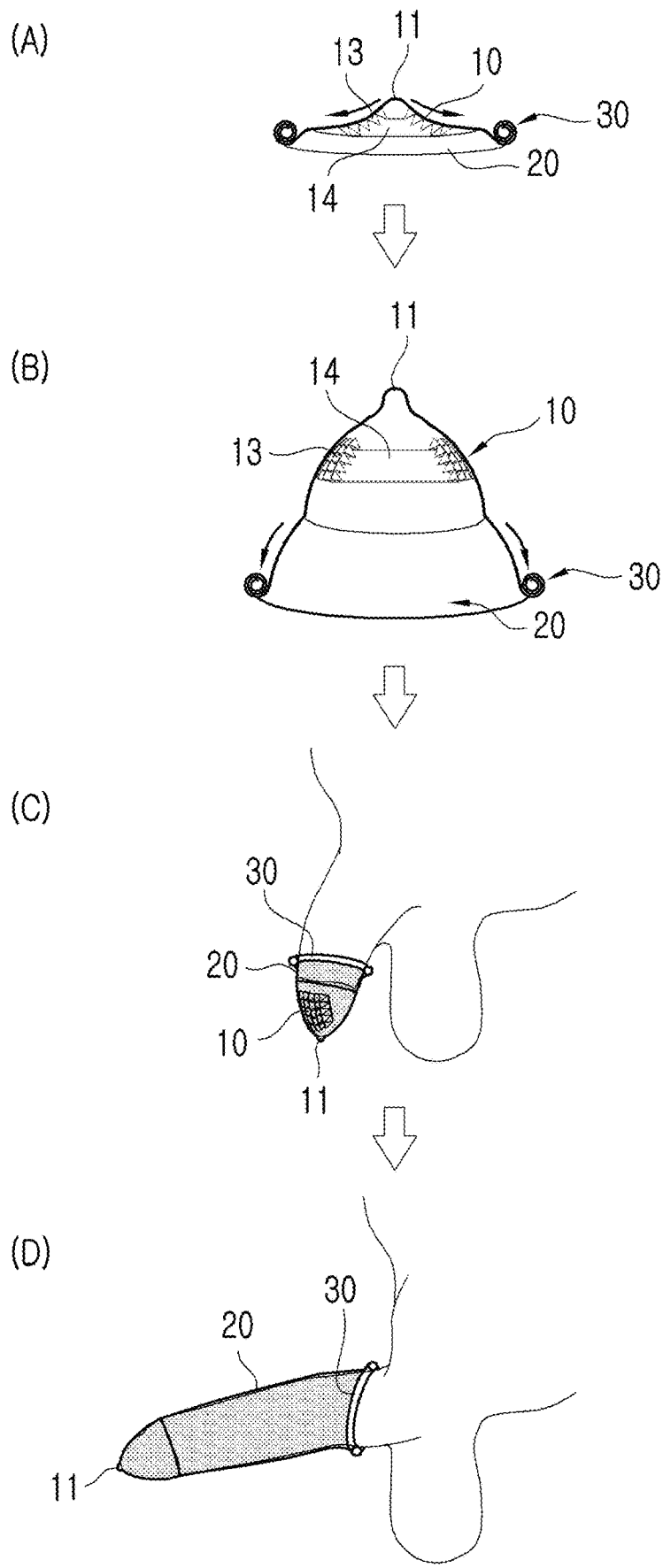
FIG. 4 is a view illustrating a method for wearing a condom according to the present invention.

A method of wearing the condom according to the present invention will be described with reference to FIG. 4, as follows.

Similarly to general condoms, the condom according to the present invention in a flattened state is packed in a wrapper (A), and a user peels off the wrapper and inflates the upper portion (10) so as to wear the condom. Further, the user removes the micro-needle cover (14) covering the micro-needles (13). For this purpose, a removal string (not shown) connected to the micro-needle cover (14) may be provided. When the user grips and pulls the removal string (not shown), the micro-needle cover (14) is separated from the micro-needles (13) and thus the condom may be in a usable state.

Thereafter, when the user wears the condom, the drug (P) included in the micro-needles (13) is administered to the user through the glans (C), and the micro-needles (13) are degraded or are absorbed into the skin of the penis simultaneously with erection.

Embodiment 2

Figure 2:
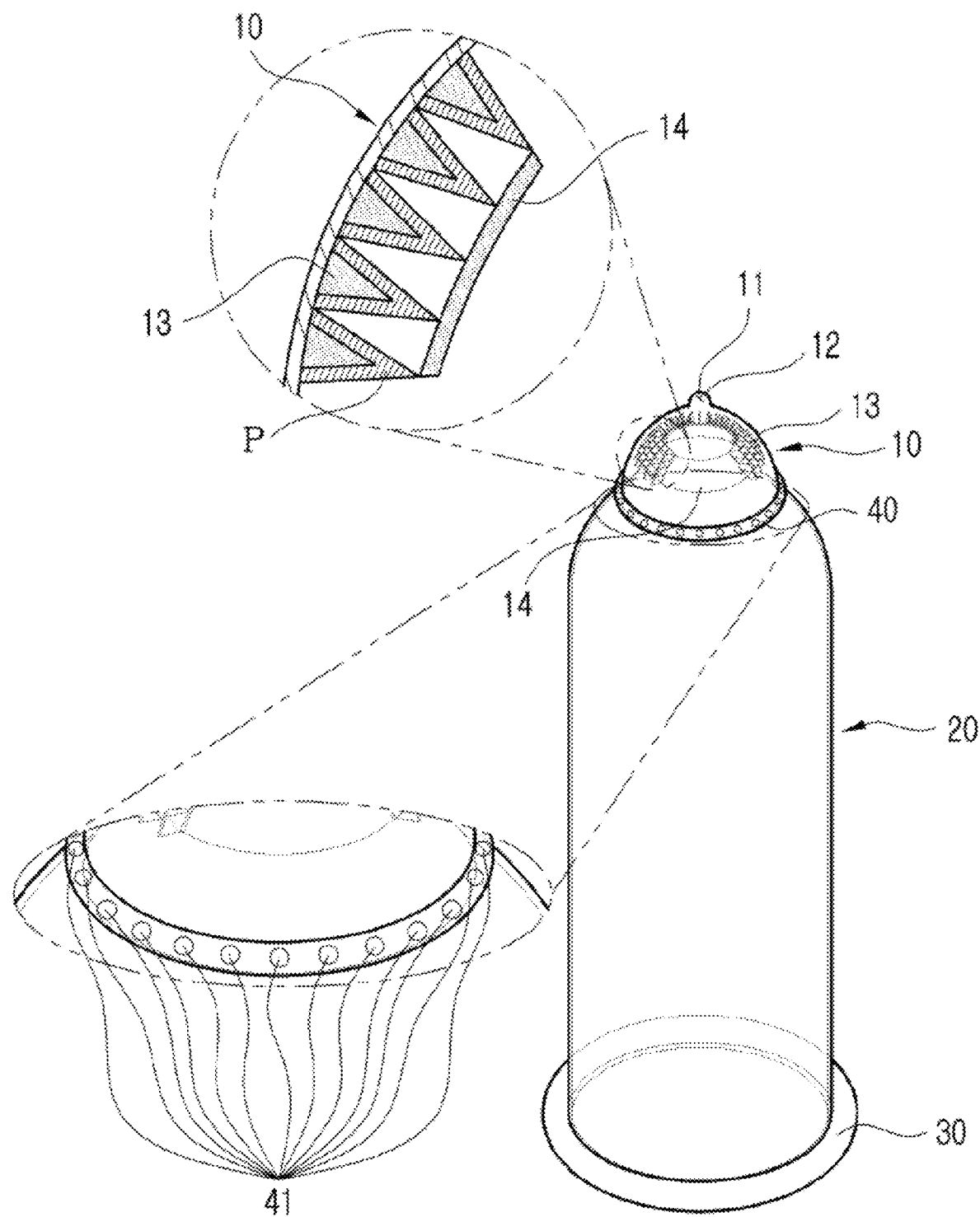
FIG. 2 is a view illustrating a condom according to embodiment 2 of the present invention.

Referring to FIG. 2, a condom according to embodiment 2 will be described.

The condom according to embodiment 2 includes micro-needles (13) so as to have a function of treating erectile dysfunction and the original function of the condom, i.e., a contraception function, in the same manner as the condom according to embodiment 1, but is different from the condom according to embodiment 1 in that the condom according to embodiment 2 further includes an intermediate tightening part (40). A detailed description of some parts of the condom according to embodiment 2, which are substantially the same as those of the condom according to embodiment 1, will be omitted because it is considered to be unnecessary.

The intermediate tightening part (40) is a ring formed of a flexible material, which is located between the upper portion (10) and the lower portion (20) of the condom.

The intermediate tightening part (40) has two functions below.

First, the intermediate tightening part (40) causes the upper portion (10) of the condom to be more firmly adhered to the user's glans so that a drug (P) included in the micro-needles (13) may be more effectively administered to the user's glans.

Since the condom according to the present invention is worn on the penis of an erectile dysfunction patient in an flaccid state, the upper portion (10) should be maximally firmly adhered to the glans of the flaccid penis so as to effectively administer the drug (P) to the glans. In the condom according to embodiment 1, the micro-needles (13) are firmly adhered to the glans due to an elastic material for the condom, but, in the condom according to embodiment 2, the intermediate tightening part (40) is provided at an intermediate part of the condom and thus further increases an adhesion degree. Therefore, the condom according to embodiment 2 may be more effective for a user having a small penis.

Second, protrusions (41) are provided on the intermediate tightening part (40) and may thus improve sexual satisfaction.

The protrusions (41) may have any shape, i.e., a bent shape, an uneven shape or the like, and stimulate the inside of the partner's vagina.

Embodiment 3

Figure 3:
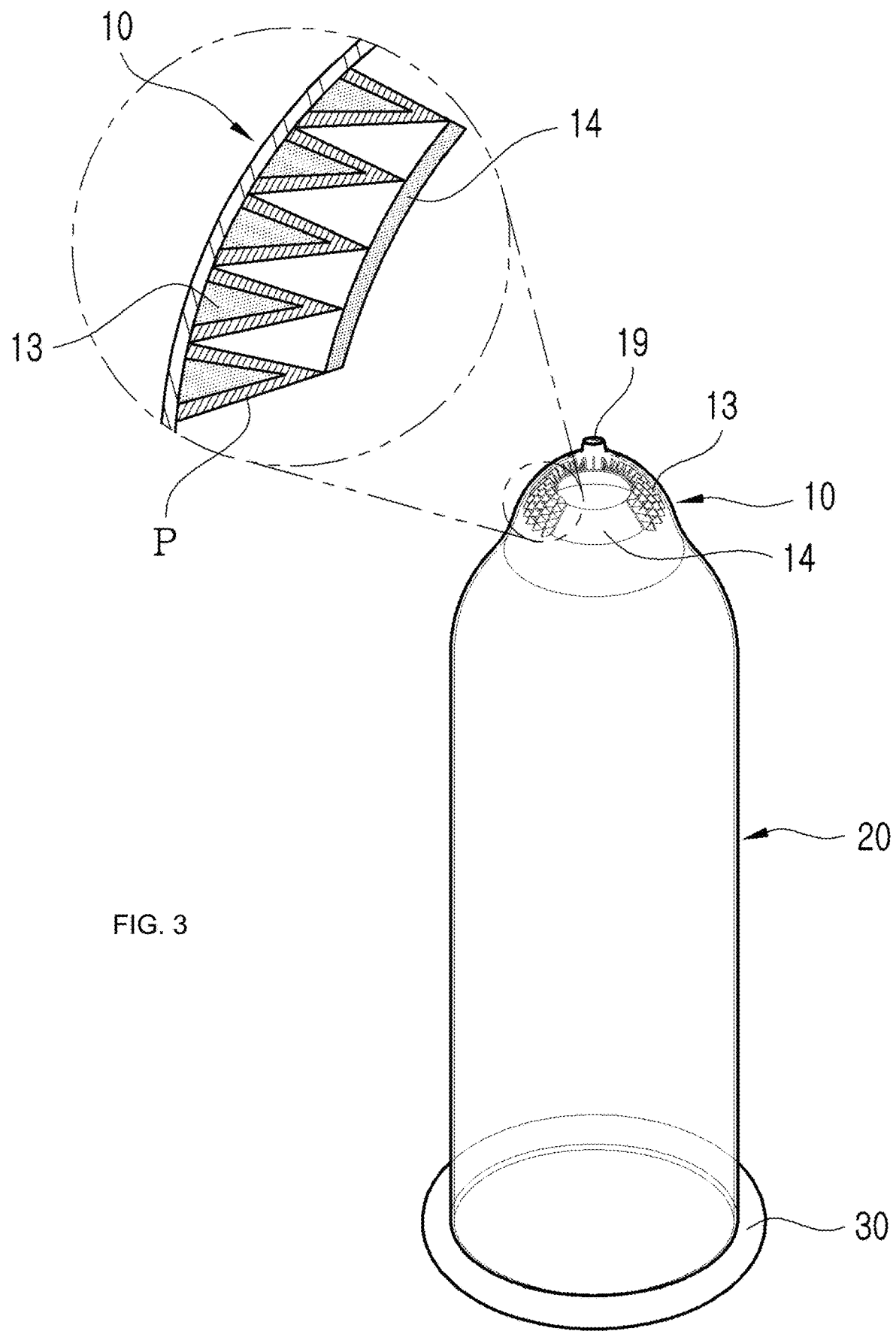
FIG. 3 is a view illustrating a condom according to embodiment 3 of the present invention.

Referring to FIG. 3, a condom according to embodiment 3 will be described.

The condom according to embodiment 3 has an intention of allowing impregnation rather than avoiding pregnancy, in contrast to the condoms according to embodiments 1 and 2. For this purpose, a distal end tip (11) is removed from an upper portion (10) of the condom, thus forming an opening (19).

When a patient with erectile dysfunction wants to impregnate his partner, if the patient wears the condom according to embodiment 1 or 2, the patient may take off the condom after he gets an erection and have sexual relations, but, if the patient wears the condom according to embodiment 3, the patient need not take off the condom after he gets an erection and may thus conveniently use the condom. That is, a user may impregnate his partner by having sexual relations while wearing the condom according to embodiment 3.

Of course, the condom according to embodiment 3 of the present invention should be provided with no spermicide, in contrast to the condoms according to embodiments 1 and 2.

Further, the upper portion (10) and the lower portion (20) may be manufactured integrally with each other so as to form one single unit, in the same manner as the condom according to embodiment 1, or an intermediate tightening part (30) may be further provided between the upper portion (10) and the lower portion (20) in a similar manner to the condom according to embodiment 2.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

DESCRIPTION OF REFERENCE NUMERALS AND MARKS

10: upper portion
11: distal end tip
12: receiving part
13: micro-needles
14: micro-needle cover
19: opening
20: lower portion
30: tightening part
40: intermediate tightening part
41: protrusions
P: drug

The invention claimed is:

1. A condom comprising:
an upper portion (10) configured to cover a glans of a user's penis, extending downwards and provided with micro-needles (13) provided on an inner surface thereof;
a lower portion (20) connected to the upper portion (10) and extending downwards; and
a tightening part (30) provided at a lower end of the lower portion (20) and configured to adhere and fix the upper portion (10) and the lower portion (20) to the penis when the condom is worn on the penis,
wherein the micro-needles (13) comprise a drug (P) corresponding to an erection inducing substance.

2. The condom according to claim 1, wherein:
the upper portion (10) extends downwards such that a radius thereof is gradually increased; and
the lower portion (20) has a greater radius than the radius of the upper portion (10) and extends downwards.

3. The condom according to claim 1, wherein the upper portion (10) is formed of an elastic material.

4. The condom according to claim 1, further comprising an intermediate tightening part (40) located between the upper portion (10) and the lower portion (20) and configured to adhere and fix the upper portion (10) to the glans.

5. The condom according to claim 4, the intermediate tightening part (40) comprises a plurality of protrusions (41) protruding to the outside of the condom.

6. The condom according to claim 1, wherein the drug (P) is one selected from the group consisting of prostaglandin (E1), papaverine and phentolamine, or is a mixture of two or more selected from the group consisting of prostaglandin (E1), papaverine and phentolamine.

7. The condom according to claim 1, having a bell shape when inflated.

8. The condom according to claim 1, wherein an opening (19) is located at a distal end tip of the upper portion (10).

9. The condom according to claim 1, wherein the micro-needles (13) are located only at a designated angle radially from a center of the upper portion (10).

10. The condom according to claim 9, wherein the micro-needles (13) located only at the designated angle radially from the center of the upper portion (10) are inserted into the glans except for a urethral meatus of the glans.

11. The condom according to claim 1, wherein the micro-needles (13) are formed of a biodegradable material.

12. The condom according to claim 1, further comprising a micro-needle cover (14) detachably attached to the micro-needles (13) so as to cover the micro-needles (13).

13. The condom according to claim 1, wherein, when the condom is worn on the penis, the micro-needles (13) are adhered to the glans, and the erection inducing substance is injected into corpus spongiosum of the glans, is then transmitted to corpus cavernosa through vein connection passages between the corpus spongiosum and the corpus cavernosa and thus causes erection.

14. The condom according to claim 1, wherein the tightening part (30) prevents blood in the penis from returning to the inside of a systemic vein and thus increases a residence time of the injected erection inducing substance in the penis.

* * * * *